United States Patent [19]

Fixel

[11] Patent Number: 4,732,180

[45] Date of Patent: Mar. 22, 1988

[54] WIRE TIE APPARATUS

[76] Inventor: Irving E. Fixel, 111 N. 31st Ave., Hollywood, Fla. 33021

[21] Appl. No.: 877,131

[22] Filed: Jun. 23, 1986

[51] Int. Cl.$^4$ ............................................. B21F 15/04
[52] U.S. Cl. ..................................... 140/119; 140/120
[58] Field of Search ................. 140/93 A, 93.6, 102.5, 140/118, 119, 120, 122, 123.5, 150

[56] References Cited

U.S. PATENT DOCUMENTS

| | | | |
|---|---|---|---|
| 1,477,766 | 12/1923 | Pulis | 140/119 |
| 2,048,437 | 7/1936 | Dolson | 140/120 |
| 2,214,267 | 9/1940 | Bednarek | 140/123.5 |
| 2,687,752 | 8/1954 | Diggs | 140/119 |
| 2,943,650 | 7/1960 | Rubin | 140/120 |

*Primary Examiner*—Lowell A. Larson
*Attorney, Agent, or Firm*—Richard M. Saccocio

[57] ABSTRACT

Apparatus for wire wrapping or tying is disclosed, wherein an inner sleeve is telescopically positioned within an outer sleeve, each of which is provided with a handle for imparting relative rotational movement. The wire tie apparatus is adapted to receive wire which is wrapped an object to be tied. The wire passes through the outer sleeve then through the inner sleeve. Apparatus is provided to fricitionally lock the wire at some point along the length of the inner sleeve. Rotation of the inner sleeve relative to the outer sleeve in accordance with specially prepared ends of both the inner and outer sleeves causes the wire to twist and to become wrapped tightly around the object to be wrapped. Further relative rotation causes inelastic extension of the wire and subsequent breakage of the same somewhere along the length of the twisted portion thereof.

7 Claims, 6 Drawing Figures

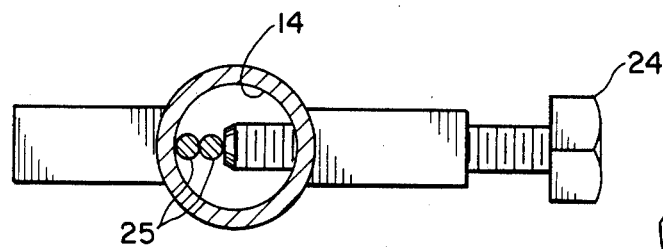
FIG.2
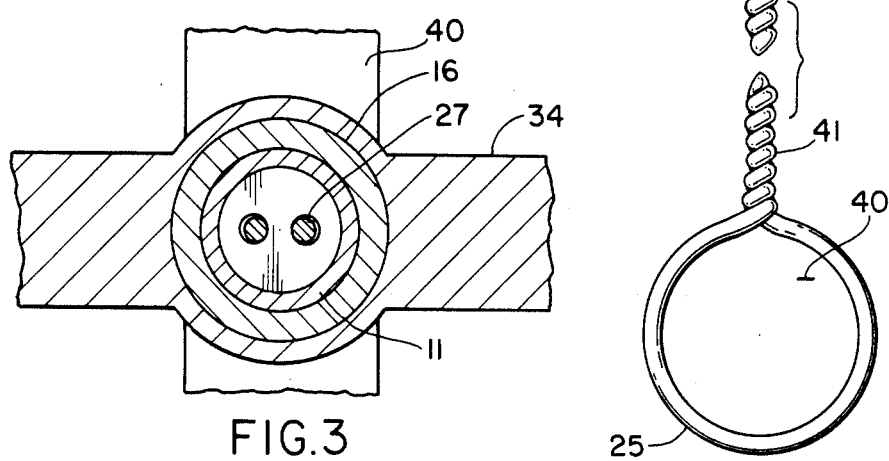
FIG.3
FIG.5
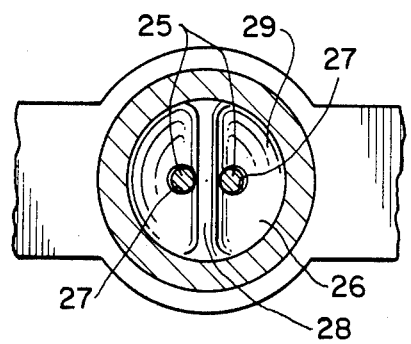
FIG.4
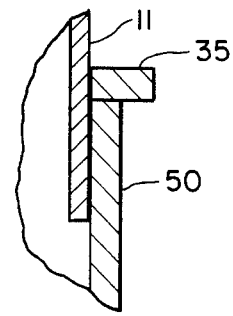
FIG.6

WIRE TIE APPARATUS

BACKGROUND OF THE INVENTION

1. Field of the Invention

This invention relates in general to the field of wire tie apparatus and in particular to the field of apparatus for wrapping an object with a wire tie whereby a tight wire wrap is created.

2. Description of the Prior Art

There are numerous occasions whereby it is desirous to wrap two portions of a generally circular object such as a bone which may be fractured on an oblique angle to the longitudinal center line of the bone. Or, to safety wire together the heads of a number of bolts whereby the bolts cannot be loosened by, for example, vibrations. Or, to fasten a rubber sleeve to a pipe such as are generally encountered situations where a hose clamp is utilized. Or, to join soft tissue such as to close a wound. Or, to merely hold together two separate pieces of any shape by a wire tie for temporary or permanent repairs such as in dentistry, automobile, or even househould repairs. This later use may, for example, comprise such situations where a broken Vee belt may be joined together at the broken ends or to substitute for a broken hanger clamp or to wire wrap a bundle of tubular members or pipes. Accordingly, there are a vast number of instances whereby it is desired to use a wire to tightly wrap one or more objects together.

In the past, a number of different apparatus have been used to attempt to create such wire wrapping. In one prior art application, the wire may be simple wrapped around the objects and hand twisted about itself at the loose ends. A slightly improved prior art method utilizes a pair of common pliers to twist the loose ends. Another prior art apparatus comprises a specially designed pair of pliers whereby the jaws may be clamped onto the loose ends of the wire which are then rotated by pulling an elongated screw member which causes racheting rotation of the jaws. Such prior art devices all suffer from numerous problems, one of which is the ability to create a tight wrap of the wire. The mechanical prior art devices can create a tight wire wrap, but only in or with respect to those applications for which the apparatus is particularly designed to work with. Such devices, however, tend to be large and bulky which preclude use in those instances where space is limited. There is, however, no prior art device which can be satisfactorily used in a large variety of applications and with a large variety of objects and things to be joined.

Accordingly, it is an object of the present invention to provide wire tie apparatus which will produce a tight wire wrap in virtually all applications where such wire wrapping is desirous.

Another object of the present invention is to provide wire tie apparatus which is relatively small, easy to use, and inexpensive to manufacture.

Another object of the present invention is to provide wire tie apparatus which is adaptable to automatic machine operations.

The above-stated objects as well other objects which although not specifically stated, but are intended to be included within the scope of the present invention, are accomplished by the present invention.

SUMMARY OF THE INVENTION

The inventive wire tie apparatus disclosed herein comprises a hand-operated device whereby a wire of any desired size, strength and flexibility may be used to secure together one or more objects. In use, the wire is wrapped around or through the one or more objects to be secured together, the free ends of the wire are then inserted and affixed to the device. Rotation of a rotatable member relative to a stationary member causes the wire to twist upon itself until such time that the wire wrap becomes tight and the wire breaks along the twisted portion thereof, leaving a "pigtail" having a number of twists. The number of twists is variable in accordance with the length of pigtail which is desired.

An inner sleeve having turning apparatus attached thereto is rotatably fitted within an outer sleeve member. A handle or grasping device is attached to the outer sleeve. The wire to be tied is fitted within the open end of the outer sleeve and into a specially prepared opening within the end of the inner sleeve and then up through the inner sleeve exiting therefrom through the other open end. The object to be tied by the wire is fitted within a loop formed at the open end of the outer sleeve. The wire is pulled through the open end of the inner sleeve and at the same time the open end of the outer sleeve member is brought up as close as possible in contact with the wire wrapped around the object to be tied. A screw affixed transversely to the inner sleeve member is tightened whereby the wire within the inner sleeve is caused to be locked within the inner sleeve member.

The handle or grasping device, which is threadingly connected to the inner sleeve, is then rotated while the outer sleeve is held in position. The inner sleeve does not rotate because of the wire. This rotation causes an extending of the inventive tie wire apparatus between the object to be wire tied and the point on the wire which is mechanically locked within the inner sleeve. In this manner, the slack in the wire around the object to be secured thereby is removed. Specially prepared slots within the open end of the outer sleeve allow the wire to fit therein such that the outer sleeve member is in contact with the object to be wire tied.

The inner sleeve is then rotated while the outer sleeve and the handle are held fixed in position. This relative motion causes the wire to twist between the length defined by the opening at the end of the inner sleeve and the location on the periphery of the object to be wire tied at the position of the end of the outer sleeve. Continued relative rotation of the portions of the inventive wire tie, causes further twisting of the wire between the aforementioned length and elimination of any remaining slack in the wire around the object to be tied. Even further turning of the relative parts of the inventive apparatus once all the slack has been removed then causes an stretching of the wire between the aforementioned length. Eventually, the wire will break due to its inability to further stretch, leaving a short length of pigtail of the twisted ends of the wire. And, of course, the object to be wire tied is tightly wire tied.

The entrance end of the inner sleeve is provided with an end plug having two openings therethrough. The openings are closely spaced with a very thin web therebetween. Further, the entrance end of each of the openings is provided with a concave surface to facilitate the entering of the free ends of the wire within and through the inner sleeve. The web assures that the wire will twist between the end of the inner sleeve and the periphery on the object to be tied.

Various other objects, advantages and features of the invention will become apparent to those skilled in the art from the following discussion taken in conjunction with the following drawings, in which:

BRIEF DESCRIPTION OF THE DRAWINGS

FIG. 2 is a cross-sectional view through the line 2—2 of FIG. 1;

FIG. 3 is a cross-sectional view through the line 3—3 of FIG. 1;

FIG. 4 is a view of the entrance end of inner sleeve taken along the line 4—4 of FIG. 1;

FIG. 5 is a schematic rendering of a wire tie as obtained by the inventive device wrapped around an object to be tied and the broken portion of the wire; and, FIG. 6 is a partial section of the inventive apparatus, illustrating another embodiment thereof.

DESCRIPTION OF THE PREFERRED EMBODIMENTS

Figure 1:
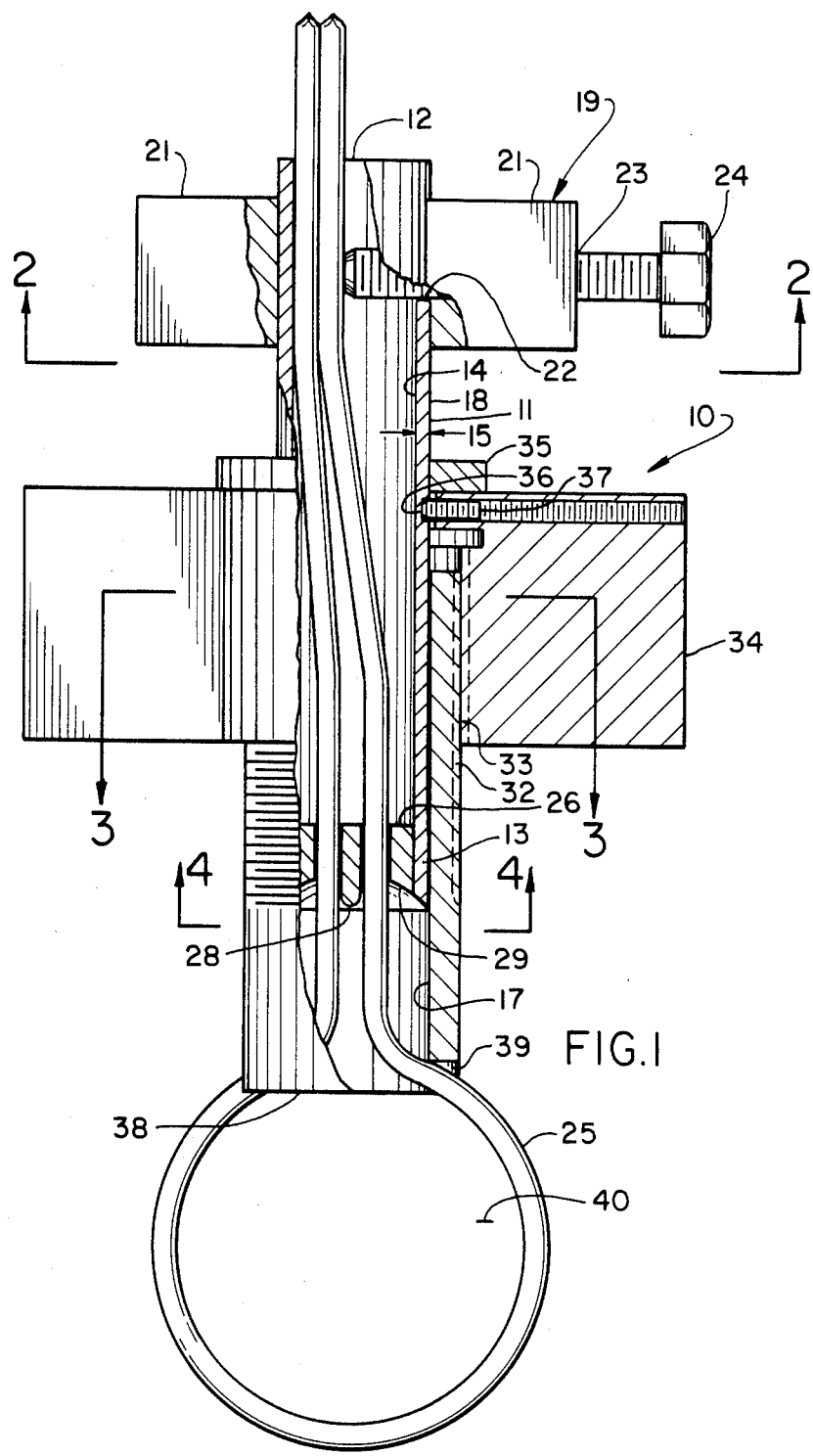
FIG. 1 is a schematical cross-sectional view of one embodiment of the inventive apparatus.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings wherein like characteristics and features of the present invention shown in the various figures are designated by the same reference numerals.

FIG. 1 schematically illustrates one embodiment of an assembly of the various components of the inventive wire tie apparatus with the wire to be applied by the apparatus wrapped around a typical object to be wire tied and threaded through the inventive apparatus. FIGS. 2 through 4 generally show transverse views of the apparatus shown in FIG. 1 at various points along the length of the assembled parts. FIG. 5 schematically illustrates a resulting wire tie and breakage from the held portion of the wire as accomplished by the inventive apparatus.

The inventive wire tie apparatus 10 comprises an inner sleeve 11, which in turn comprises an elongated tubular member having an open outlet end 12 and a capped entrance end 13. The internal diameter 14 of inner sleeve 11 is appropriately sized such that it will conveniently fit side-by-side lengths of the wire to be utilized with the device. For example, inner diameter 14 may be sized to be the approximate equivalent of three times the outer diameter of the maximum sized wire to be utilized with the inventive apparatus 10. The wall thickness 15 of inner sleeve 11 is not critical to the invention but should be of sufficient thickness such that adequate tubular rigidity is achieved. It is to be noted, however, that the inner diameter 17 of outer sleeve 16 is determined by the outer diameter 18 of inner sleeve 11 because of the telescoping fit of inner sleeve 11 within outer sleeve 16.

A knob or other appropriate turning means 19 is fixedly connected to inner sleeve 11 near the outlet end 12 thereof. In the embodiment shown in the drawings, turning means 19 comprises a pair of wings 21 fixedly connected to opposite sides of the inner sleeve 11. The function of turning means 19 is to enable rotation of inner sleeve 11. Accordingly, turning means 19 may comprise any appropriate shape capable of imparting rotational motion to inner sleeve 11. For example, another appropriate shape, although not shown, may comprise a hexagonal nut or cylinder having a pair of oppositely disposed flats machined thereon, so that turning may be effectuated either by hand or by the use of a wrench fitted to the machine flats. Other appropriate shapes may be readily envisioned. An opening 22 is provided through the wall of inner sleeve 11 in alignment with another opening 23 through one of the wings 21 in the manner shown in the drawings. Opening 23 is threaded to allow screw 24 to be fitted therein. Screw 24 passes through opening 22 in inner sleeve 11 and is used to frictionally or mechanically lock the parallel lengths of wire 25 passing within and through inner sleeve 11. Such mechanical locking is also and perhaps more clearly shown in FIG. 2 of the drawings.

A cap 26 is fixedly attached to or integrally provided with inner sleeve 11 at the entrance end 13 of inner sleeve 11. Cap 26 includes a pair of parallel arranged axial openings 27. The diameter of each of the openings 27 is sized slightly larger than the outer diameter of the maximum sized wire 25 to be used. A thin web 28 is provided between openings 27 which results from the spacing provided between the openings 27. The entrance portion of each opening 27 is provided with a sloped or concave surface 29, which is also shown in FIG. 4 of the drawings, and which is used to facilitate the respective entering of the free ends of wire 25 through openings 27 and into inner sleeve 11. Surfaces 29 may be made by countersinking each hole 27 with appropriate countersinking drills, by a numerically controlled and grinding machine, by hand grinding, or by any other well known metal working method or machine. In this manner, the free ends of wire 25 may be cut by any appropriate tool which may incidentally leave a sharp or jagged end. The surfaces 29 allow wire 25 having such sharp or jagged ends to easily enter openings 27 without the need to eliminate the sharp or jagged ends. By providing the entrance end of cap 26 with such a configuration, two conventionally cut free ends of wire 25 may be inserted within outer sleeve 16 and by the use of very slight pushing force, each end of wire 25 will automatically find one of openings 27 and simply slide within inner sleeve. Thus, fitting of the free ends of wire 25 to and within inner sleeve 11 is accomplished by the inventive apparatus 10 without the need to disassemble outer sleeve 16 to expose end 13 of inner sleeve 11 and to individually fit each free end in openings 27. In this regard, however, it is to be noted that the inner diameter 17 of outer sleeve 16 should be only slightly greater than the outer diameter 18 of inner sleeve 11 so that the cut ends of wire 25 do not hang up on the clearance space between the sleeves.

Outer sleeve 16 also comprises an elongated cylindrical member having a wall of sufficient thickness to provide the same with sufficient rigidity. A handle means 34 is threadingly connected to outer sleeve 16 by male threads 32 and female threads 33 and is located at the remote end of outer sleeve 16. Handle means 34 may comprise a hexagonal nut or an elongated bar having a cylindrical center portion with oppositely disposed wings extending therefrom. The actual shape of handle means 34 is relatively unimportant providing that the shape which is chosen allows for convenient grasping of the apparatus and turning relative to inner sleeve 11 and outer sleeve 16. An annular member or a flange 35 is fixedly connected to inner sleeve 11, such as by welding, silver soldering, or other appropriate well-known method and is located between turning means 19 and entrance end 13 of inner sleeve 11. Flange 35 limits the amount of axial telescoping of outer sleeve 16 relative to inner sleeve 11 and provides for elimination of slack associated with wire 25 before twisting is commenced. If desired, a cylindrical cutout 36 around the outer periphery of inner sleeve 11 in conjunction with a set screw 37 threadingly connected within handle 34 may be used to prevent axial disengagement of handle 34 from inner sleeve 11 while allowing relative rotational motion.

As previously noted, outer sleeve 16 is threadingly connected 33 to handle means 34. Rotation of handle means 34 relative to outer sleeve 16 and inner sleeve 11, such as when handle means 34 is rotated and both inner sleeve 11 and outer sleeve 16 are held stationary, thereby results in increasing or decreasing the distance between the open end 38 of outer sleeve 16 and the point at which screw 24 mechanically locks wire 25 within inner sleeve 11. This variation in length, as will be more fully explained later, provides for the final removal of slack from wire 25 as it is wrapped around the object to be tied and before twisting of the wire begins. Open end 38 of outer sleeve 16 is provided with a pair of diametrically opposed slots 39. The cross-sectional opening of each of slots 39 is slightly greater than the outer diameter of wire 25 to be used with the inventive apparatus 10. By appropriately aligning outer sleeve 16 with wire 25, each side of wire 25, as it makes the transition from around the object to be tied into outer sleeve 16, is thereby fitted within its respectively located slot 39. The fitup of wire 25 in slots 39 thus prevent rotation of outer sleeve 16 and allows the open end 38 of outer sleeve 16 to be positioned firmly against the object to be tied or wire wrapped. While the inventive apparatus can function without the use of slots 39, their presence enhances the operation of the wire tie apparatus 10 and improves the tightness of the resulting wire tie.

In order to effectuate a wire tie or wrap, of any appropriate object or objects, the following procedure may be utilized. An appropriate length of wire 25 of appropriate strength, hardness, size, and material is selected such that it is long enough to fit around object 40 and within and through the inventive apparatus 10. Wire 25 may, for example, comprise wire made from mild steel so that it may readily conform to the outer periphery of the object 40 to be tied. The cut ends of wire 25 are then brought together forming a loop at the middle thereof. The loop is wrapped around the object 40 to be tied and the free ends of wire 25 are inserted within the open end 38 of outer sleeve 16. At this point, outer sleeve 16 may be threadingly and fully engaged within the threaded opening of handle 34. While holding both handle means 34 and turning means 19, the free ends of wire 25 are then pushed up until contact is made with the capped end 13 of inner sleeve 11. By using a slight pushing force and, if necessary, a slight rotation of inner sleeve 11, the free ends of wire 25 will automatically find openings 27 and pass therethrough into inner sleeve 11 and emerge out of end 12 thereof. The free ends of wire 25 may then be grasped by hand and while holding onto the inventive apparatus 10, wire 25 may be pulled further through the inventive apparatus 10 while moving the wire tie apparatus toward object 40. At this time, end 38 of outer sleeve 16 should be approximately in contact with the outer periphery of the object to be tied 40 and each side of wire 25, is fitted within its respective slot 39. Also at this time, substantially all of the slack of the wire 25 around object 40 and within wire tie apparatus 10 should be eliminated by pulling the free ends of wire 25 away from object 40 and simultaneously pushing apparatus 10 toward object 40. While maintaining the relative position of the inventive apparatus 10, wire 25 and object 40, screw 24 is turned such that the parallel portion of wire 25 is mechanically locked within inner sleeve 11. At this point of the procedure, a fixed length of wire 25 is established between the screw 24 and the outer periphery of object 40. This length should also be substantially equal but slightly more than the distance between screw 24 and end 30 of the outer sleeve 16. While maintaining the relative rotational position of inner sleeve 11 and outer sleeve 16 to each other and to wire 25 and object 40, handle 34 is rotated to further extend outer sleeve 16 from handle 34. The abutting contact of handle 34 with flange 35 in combination with the rotation of handle 34 also causes an extension of outer sleeve 16 relative to inner sleeve 11; that is, the length between end 12 and end 38 increases. The rotational motion of handle 34 is continued until such time as any remaining slack has been removed from wire 25 around object 40 and at the location of the entrance of wire 25 within outer sleeve 16. Also, because wire 25 is mechanically locked by screw 24, outer sleeve 16 is firmly positioned against object 40. Outer sleeve 16 may if desired be provided with a knurled or fluted surface or other appropriate configuration to facilitate it being held in position while handle 34 is being rotated. However, for most applications, a smooth outer surface is satisfactory.

At this point in the operational sequence, the actual twisting of the wire is to be effectuated. This is accomplished by holding handle 34 while rotating turning means 19. Because wire 25 is fitted within slots 39, outer sleeve 16 is thereby prevented from rotation when turning means 19 is rotated. If no slots 39 are provided, the firm positioning of outer sleeve 16 against wire 25 and object 40, prevents rotation of outer sleeve 16 when turning means 19 (and inner sleeve attached thereto) is rotated. Continued rotation of turning means 19, which, of course, causes rotation of inner sleeve 11, causes the length of wire between end 13 and end 38 to twist. Since the length of wire 25 is fixed as explained above between screw 24 and end 38, twisting of the wire 25 causes it to tightly wrap around object 40. The tightness of the wrapping continues to increase with further twisting of the wire by rotating turning means 19 until the point is reached whereby no further tightening of the wrap can occur and then elastic extension of the wire between the approximate midpoint of the length between end 13 and end 38 begins to occur. Continued rotation of turning means 19 causes the elastic extension to become inelastic extension and ultimately the wire breaks. The wire break uniformly occurs at the approximate midpoint along the length of the wire twists. At this time, the inventive apparatus and the broken portion of the wire within the inventive apparatus 10 is released from the object 40. There results a wire wrapped object as shown schematically in FIG. 5. A twisted length of pigtail 41 extends from the wrapped object 40. Pigtail 41 may then be left as it is or bent along any line not detrimental to the position of function of the wire wrapped object 40. A shorter or longer length of pigtail 41 may be obtained by increasing or decreasing, respectively, the distance between end 13 of inner sleeve 11 and end 38 of outer sleeve 16 prior to mechanically locking wire 25 by screw 24.

FIG. 6 shows an alternate embodiment whereby the handle 34 of the embodiment of FIG. 1 is eliminated. In this embodiment, the telescopic engagement of inner member 11 and outer member 50 is non-adjustable and is fixed by the axial position of flange 35.

It is to be noted that the above-described and disclosed apparatus can be adapted to automatic machine operations whereby the handle 34 and the turning means 19 may be respectively attached to stationary and rotatable apparatus which apparatus then functions in a manner similar to the hand operations described above.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim as my invention:

1. Wire tie apparatus adapted to wire wrap an object or to wire wrap objects to be tied together comprising
    a first cylindrical member having a first end abutting said object or objects to be tied
    a second cylindrical member positioned within said first cylindrical member and extending out from a second end thereof
    said first and second cylindrical members being arranged for relative axial movement therebetween
    a pair of spaced side-by-side substantially coextending openings at the end of said second cylindrical member within said first member adapted to respectively receive ends of a loop of said wire
    means for securing the ends of said wire to said second member at a location axially spaced from an entrance of said spaced apart openings
    means for rotating said inner member, and said wire secured thereto, relative to said outer member whereby said wire is twisted between the entrance end of said spaced apart openings and said first end of said outer member and whereby said twisted wire breaks therebetween when the wire wrapping of the object or objects is complete, and
    means for adjusting the axial position of said first end of the outer cylindrical member relative to the end of said inner member within the outer member and having said spaced apart openings whereby the length of twisted wire remaining after said twisted wire breaks is adjustable.

2. The wire tie apparatus of claim 1, further comprising means for fixing the axial position of said second member relative to said first member whereby the first end of said first member abuts the object or objects to be tied, comprising a flange member fixedly attached to and extending from the outer surface of said second member, said flange member being in abutting engagement with said second edge of said first member.

3. The wire tie apparatus of claim 1, further comprising means for fixing the axial position of said second member relative to said first member whereby the first end of said first member abuts the object or objects to be tied, comprising a flange member fixedly attached to and extending from the outer surface of said second member, and a rotatable member threadingly attached to said second end of said first member, whereby rotation of said rotatable member relative to said first and second members adjusts the length of the axial engagement of said first and second members and whereby abutting engagement of said rotatable member and said flange member fixes said length of said axial engagement.

4. The wire tie apparatus of claim 1, wherein the entrance end of said spaced apart openings are each provided with a separate inwardly sloping surface whereby the ends of said wire are respectively directed to enter said openings when inserted through said first end of said first member.

5. The wire tie apparatus of claim 1, wherein said means for securing the ends of said wire to said second member comprises a threaded opening through the thickness of said second member, a screw threadingly engaged in and through said threaded opening, whereby the ends of said wire within said second member are pressed together between an inner surface of said second member and the end of said screw within said second member.

6. The wire tie apparatus of claim 1, wherein said first end of said first member includes a pair of circumferentially opposed slots through the wall of said first member for receiving opposing portions of said wire at the location where the wire is to be twisted.

7. The wire tie apparatus of claim 1, further comprising turning means for rotating said second member, and said wire secured thereto, relative to said first member whereby said wire is twisted between said entrance end of said spaced openings and the first end of said first member and subsequently breaks therebetween when the wire wrapping of the object or objects is complete, said rotating means comprising a knob member attached to said second member.

* * * * *